(12) United States Patent
Ringold et al.

(10) Patent No.: US 11,998,333 B2
(45) Date of Patent: Jun. 4, 2024

(54) DEVICE AND SYSTEM FOR PRESERVING ANALYTES IN BLOOD SAMPLES DURING STORAGE AND TRANSPORTATION

(71) Applicants: VDI Laboratory, LLC, Simi Valley, CA (US); KEPLER DIAGNOSTICS, INC., Simi Valley, CA (US)

(72) Inventors: Randy Ringold, West Hills, CA (US); Tyson Ringold, Toronto (CA)

(73) Assignee: VDI Laborary, LLC., Chatsworth, CA (US)

(*) Notice: Subject to any disclaimer, the term of this patent is extended or adjusted under 35 U.S.C. 154(b) by 764 days.

(21) Appl. No.: 16/622,140

(22) PCT Filed: Aug. 3, 2018

(86) PCT No.: PCT/US2018/045287
§ 371 (c)(1),
(2) Date: Dec. 12, 2019

(87) PCT Pub. No.: WO2019/240829
PCT Pub. Date: Dec. 19, 2019

(65) Prior Publication Data
US 2021/0401411 A1 Dec. 30, 2021

Related U.S. Application Data

(63) Continuation of application No. PCT/US2018/037302, filed on Jun. 13, 2018.
(Continued)

(51) Int. Cl.
*A61B 5/00* (2006.01)
*A61B 5/15* (2006.01)
(Continued)

(52) U.S. Cl.
CPC .. *A61B 5/150358* (2013.01); *A61B 5/150305* (2013.01); *A61B 10/0096* (2013.01);
(Continued)

(58) Field of Classification Search
None
See application file for complete search history.

(56) References Cited

U.S. PATENT DOCUMENTS 4,308,148 A   12/1981  Boutin et al.
5,354,692 A * 10/1994  Yang ................... G01N 33/558
                                                              436/805

(Continued)

FOREIGN PATENT DOCUMENTS

EP        0806666 A2   12/1997
EP        1174716 A2    1/2002
WO   WO2016/070971 A1   5/2016

*Primary Examiner* — Jyoti Nagpaul

(57) ABSTRACT

Freshly obtained blood samples are deposited into a device that contains blood sample carriers, each of the carriers is designed to hold a fixed amount of blood and allow excess blood sample to flow through and be discarded. A desiccant within the blood sample carrier aids with the drying of the blood and the discarding of the excess sample blood. The device is stored/transported within a modified atmosphere package comprised of an impermeable sealable bag and an oxygen scavenger compound for removing oxygen from the bag.

18 Claims, 7 Drawing Sheets

Related U.S. Application Data

(60) Provisional application No. 62/519,171, filed on Jun. 13, 2017.

(51) Int. Cl.
  *A61B 10/00* (2006.01)
  *B01L 3/00* (2006.01)
  *G01N 1/30* (2006.01)

(52) U.S. Cl.
  CPC .............. *B01L 3/5021* (2013.01); *B01L 3/505* (2013.01); *G01N 1/30* (2013.01); *A61B 2010/0006* (2013.01); *B01L 2200/18* (2013.01); *B01L 2300/0618* (2013.01); *B01L 2300/0809* (2013.01); *B01L 2300/105* (2013.01); *B01L 2300/123* (2013.01); *B01L 2300/126* (2013.01)

(56) References Cited

U.S. PATENT DOCUMENTS

| | | | |
|---|---|---|---|
| 8,417,312 B2 * | 4/2013 | Kamath | A61B 5/7264 600/347 |
| 10,145,840 B2 * | 12/2018 | Patwardhan | B01L 9/52 |
| 2012/0090275 A1 | 4/2012 | Uchida et al. | |
| 2017/0059551 A1 | 3/2017 | Patwardhan et al. | |

* cited by examiner

DEVICE AND SYSTEM FOR PRESERVING ANALYTES IN BLOOD SAMPLES DURING STORAGE AND TRANSPORTATION

CROSS-REFERENCES TO RELATED APPLICATIONS

The present application is a national phase application of international patent application number PCT/US18/45287, filed on Aug. 3, 2018, which is a continuation-in-part of the PCT application No. PCT/US18/37302 filed on Jun. 13, 2018, which is in turn claims priority to U.S. provisional patent application No. 62/519,171 filed on Jun. 13, 2017, the content of each of referenced applications is included herein its entirety by reference.

FIELD OF THE INVENTION

The invention relates to a method and device for collecting and storing blood samples. More specifically, the invention comprises a device and system for receiving a freshly obtained blood sample, drying the blood sample and maintaining blood characteristics until blood is recovered for testing of analytes.

BACKGROUND OF THE INVENTION

Clinical laboratory testing typically involves liquid whole blood and/or liquid plasma, or serum. It is thus critical to preserve the integrity of blood samples from the location and time they are drawn to the location and time they are used.

Special preservatives and/or transportation procedures to preserve specimen integrity are required as proteolytic enzymes, naturally occurring in blood, plasma or serum, can degrade proteins. Routine commercial laboratories have set up extensive logistical networks to rapidly transport specimens. This includes, for example, shipping the specimens in insulated containers with cold packs or dry ice and/or tubes with special preservatives.

In the 1960s, dried whole blood testing was launched for neonatal testing of Phenylketonuria (PKU). Using special cellulose based paper, dried blood spot cards were used to collect blood samples for PKU testing. The specimens, once dried, assisted in the preservation of this analyte. The DBS cards could be stored and transported at ambient temperature for up to two weeks, which allows for transportation by common letter mail service, thus reducing cost of transportation. Upon receipt by the laboratory, blood in the specimen is extracted and tested for PKU.

Since that time, the use of dried blood spot collection and testing has expanded to test for other analytes, provided that certain requirements are met, which include, for example, that the analyte must be in relatively high concentration; the analyte must be very stable under adverse conditions and the analyte must not require a high degree of analytical precision to be useful.

Further, other manufacturers have developed similar devices using cellulose based paper and synthetic based papers for dried blood, serum, plasma testing, herein referred to dried blood specimen (DBS), however still suffer from the same limitations.

The prior art methods and devices meet the above limitations only for those applications that can be satisfied with low precision (e.g., genetic DNA testing). However the use of DBS for routine chemistries, enzymes, or high precision and/or high sensitivity work fails to meet the required specifications. In tests that measure enzyme activity, for example, enzymes often become inactive after being dried i.e. the enzymes do not convert substrate to product. In tests that use antibodies to measure protein mass (ELISA), drying specimens causes epitopes to become hidden or 3-dimensional conformation is lost i.e. antibodies fail to bind to the target protein. In tests that require a high degree of precision or sensitivity, consistent concentration of the DBS to near neat blood levels is not achieved i.e. unable to measure low concentration of a target analyte with satisfactory precision. The fundamental problems to be solved are:

how to stabilize the specimen so enzymes would properly function how to maintain protein structure so immunoassays would properly recognize epitopes how to consistently concentrate the specimen to maintain precision and sensitivity Alternative materials, other than cellulose, have been developed. Synthetic materials have advantages over cellulose in greater recovery due to low non-specific binding. However due to the impact of specimen drying and prolonged storage (up to two weeks) at ambient temperature the inherent limitations of DBS still remain.

Another process that dries and stabilizes biological samples is lyophilization. Invented in the early 1900's, it was derived from a similar method used by the natives of the Andes. Lyophilization is a process of water removal by sublimation. Under a vacuum, liquid water is quickly frozen and the water is instantly turned into a gas and removed. The process is also known as freeze-drying.

Lyophilization is well known for its ability to preserve a wide range of biological samples. Pharmaceuticals, diagnostic reagents and calibrators, bacterial cultures, are frequently lyophilized. The end result is a dry sample that is under vacuum that can be stored. Studies performed since the nineteen sixties have shown that higher vacuum conditions result in longer storage time, presumably due to lower oxygen levels (Dewald, 1966). Because of the required logistics and the prohibitive cost, even as lyophilization is effective at sample preservation, the process is impracticable to implement as a routine use in blood sample preservation and diagnostics.

On other hand, DBS eliminates the time-sensitive nature of blood testing. It removes the high cost of packaging and shipping and allows for testing in situations that are poorly served today such as rural/undeveloped markets or home-based wellness screening. Because of these advantages, there has been a long-felt need to use DBS in testing for many analytes in blood samples. However all currently available DBS products and testing procedures do not overcome the inherent limitations of current DBS testing and thus prevents a widespread use to analytes other than the ones that meet the stability, concentration and precision limitations (as described above).

Therefore, there is a need for a device and system that provide specimen stability for storage and transportation in a way that improves servicing the healthcare needs in a cost-effective manner.

SUMMARY OF THE INVENTION

The invention provides a device for collecting blood samples, and a system including a container for creating a modified atmosphere for storing and/or transporting the device to a test laboratory. The procedure involves drying blood samples once they have been deposited in the device for collecting blood samples, and placing the device in a container (e.g., sealed bag) in which oxygen is scavenged by the presence of an oxygen scavenger.

The device for collecting and storing blood samples presents numerous advantages. The device uses absorbent paper to store a predetermined volume of blood in each sheet of paper. The device uses a layer of desiccant that acts to both dry the sample of blood and allow the excess blood (the portion that is not retained by the paper) to flow through the paper and reach the desiccant area. The latter allows a person with imprecise volume measurement to deposit a quantity of blood onto the device, but the volume of blood collected is at the end precise, because of the predetermined size of the paper, its specific absorption characteristics, and the fact that excess blood is trapped at a different level, away from the paper.

The invention provides a container for storing and transporting the device for collecting blood samples, while preserving the analytes quality in the blood sample by providing a modified atmosphere.

The challenge of preserving the freshness of biological product is encountered by the food industry i.e., maintaining moisture or modified atmospheric conditions. In the latter industry, however, the manufacturer is concerned only with the "outbound" problem (i.e. transport from manufacture to end-user); and the problem has been solved by the use of foil and/or impermeable plastic (e.g., Mylar). The manufacture simply heat seals the package ensuring a long lasting seal. Once the package is opened by the end-user there are often seals (e.g., zip lock) to provide in what may be referred as a "Freshness tight" seal. However, "Freshness tight" seals are not oxygen impermeable. Furthermore, while heat sealing provides an adequate solution to providing a modified atmospheric packaging for the outbound transportation, there is not an easy and reliable packaging for inbound (i.e., customer to laboratory) method to maintain an internal MAP. Heat sealing is not a reliable customer option due to typical lack of the equipment required or easy access thereto.

The invention provides a container for storing and shipping of blood samples. The container is made in a form a bag, having a dual track zip lock, and a flap that is made to fold and glue onto the bag in order to achieve complete seal of the bag.

DETAILED DESCRIPTION OF THE INVENTION

Figure 1:
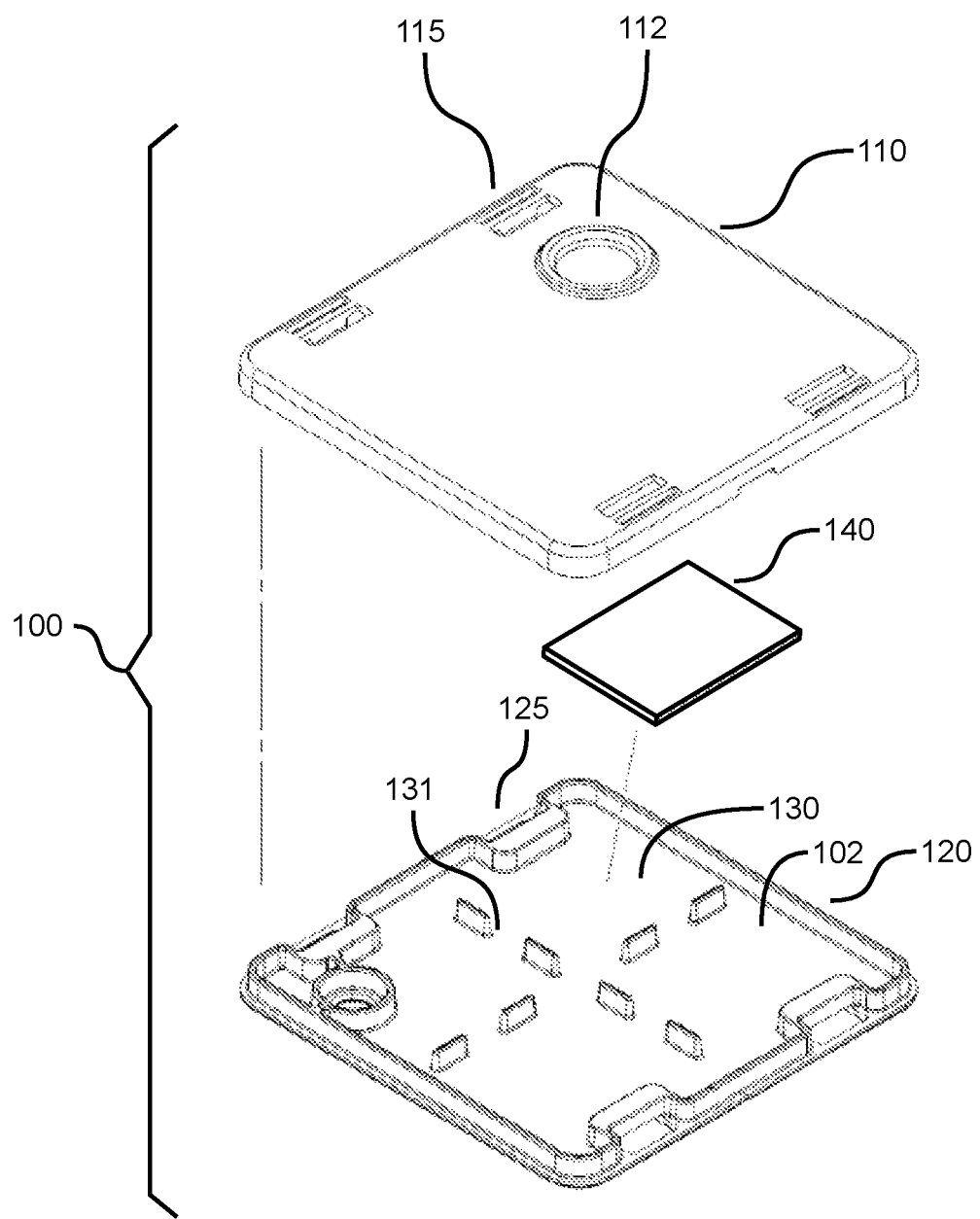
FIG. 1 represents an exploded perspective view of a device for receiving freshly collected blood samples and for drying and storing the samples in accordance with an embodiment of the invention.

The invention provides a system for drying and packaging freshly collected blood samples, storing the dried blood samples in a modified atmosphere (e.g., for transportation), and allowing for precise blood sample recovery/extraction without requiring high precision at the initial collection of samples. The system comprises a device for receiving freshly collected blood samples and drying the blood samples for long-term storage, a device for creating a modified atmosphere that preserves analytes in the dried blood samples and facilitates blood sample extraction for analyte testing. The invention also provides a method of use of the system that allows a user to collect an imprecise volume of blood, while achieving high precision of blood sample volume at recovery/extraction.

In the following description, numerous specific details are set forth to provide a more thorough description of the invention. It will be apparent, however, to one skilled in the pertinent art, that the invention may be practiced without these specific details. In other instances, well known features have not been described in detail so as not to obscure the invention. The claims following this description are what define the metes and bounds of the invention.

The present disclosure shares some aspects of the concepts and the methods described in PCT patent applications number PCT/US18/37302, which is included herein in its entirety by reference.

Terminology

Throughout the disclosure, a reference to blood sample comprises a reference to a sample of blood or whole blood including plasma and all of the cellular components such as red and white blood cells. Plasma shall refer to the liquid phase of blood less the cellular components. Serum shall mean the fluid separated from clotted blood (e.g., plasma less clotted proteins). In addition, a reference to sample, as a shorthand reference, shall refer to any of the latter terms, the specific meaning of which depends on the context in which it is used and can be easily inferred by one with ordinary skills in the art.

Dried blood, serum, plasma specimen shall refer to any means for obtaining dried samples of blood, plasma, or serum. In particular, dried blood spots (DBS) terminology is used in the field of blood testing as blood samples collected as fluid samples and deposited on an absorbent support material (also known as carrier fibers, filter paper of simply paper), the blood samples then appears as blood spots.

Neat or near neat volume shall refer to the concentration of blood components in their native liquid state. Routine blood, plasma, or serum testing begins with the sample in its native liquid state. The procedure may require a dilution prior to testing; however components that are low in concentration do not. To achieve sensitive and reproducible results the extracted fluid from the DBS needs to be at or close to neat blood, plasma, or serum level.

Modified atmosphere packaging (MAP) shall mean a system to artificially create an atmosphere separated from the ambient atmosphere and resistant to gas exchange. MAP may be a bag, container or device and made from materials that are gas impermeable such as plastic or glass.

Anti-oxidant treatment shall mean methods to remove residual molecular oxygen ($O_2$) from a modified atmosphere packaging (MAP).

The term "oxygen scavenger" is used throughout the disclosure to refer to anti-oxidant compounds known for biding (and even reacting) with molecular oxygen, which results in fixating the oxygen in a non-gaseous state.

A desiccant refers to any compound that is known to bind water molecules. Desiccant treatment shall mean methods to remove residual $H_2O$ from a modified atmosphere packaging (MAP).

Extraction (or blood extraction) shall mean the process of removing the blood components from the fiber matrix, whether cellulose, synthetic based or any other available dried blood support material.

Device for Collecting and Preserving Blood Samples

FIG. 1 represents an exploded perspective view of a device for receiving freshly collected blood samples and for drying and storing the samples in accordance with an embodiment of the invention. A device 100 according to the invention comprises a top portion 110, and a bottom portion 120, to which it may be referred for simplicity as top and bottom lids. The lids may lock to one another to provide an enclosure 102. The locking may be temporary/reversible by a close and open mechanism. In the illustration of FIG. 1, the upper lid 110 and bottom lid 120 are designed with snap locks (e.g., 115 and 125) for securely locking the top and bottom and for allowing an easy open by a user.

The locking of the lids to one another may also be permanent, as the need for any implementation may be, such as by gluing the top and bottom portions to one another.

Device 100 may be made of plastic, metal or any other material that may be required for an implementation of the invention. Top and bottom lids are preferably of matching rectangular or square shapes and have a dimension that allows the device to securely and comfortably fit in a person's hand. For example, in an embodiment of the invention the top and bottom lids are square shaped with a side dimension in the range of 2 inch to 3 inch (e.g., about 2.3 inch), and the thickness of device 100, once the lids have been locked together, about 0.2 inch.

Enclosure 102 provides one or more holding regions (e.g., 130) each one of which for holding one dried blood carrier 140. Holding regions (e.g., 130) may be separated by ridges 131. The ridges 131 play a role in securing the dried blood carriers in place and are spaced out with a plurality of channels to allow for air circulation within the enclosure to promote the drying of the blood and the reduction of free oxygen once device 100 is in the presence of an oxygen scavenger (see below for more detail).

The top lid 110 comprises one or more windows (e.g., 112) to allow a user access to deposit a blood sample onto blood sample carrier 140 placed directly under the window in a holding region (e.g., 130).

Dried Blood Sample Carrier

Figure 2:
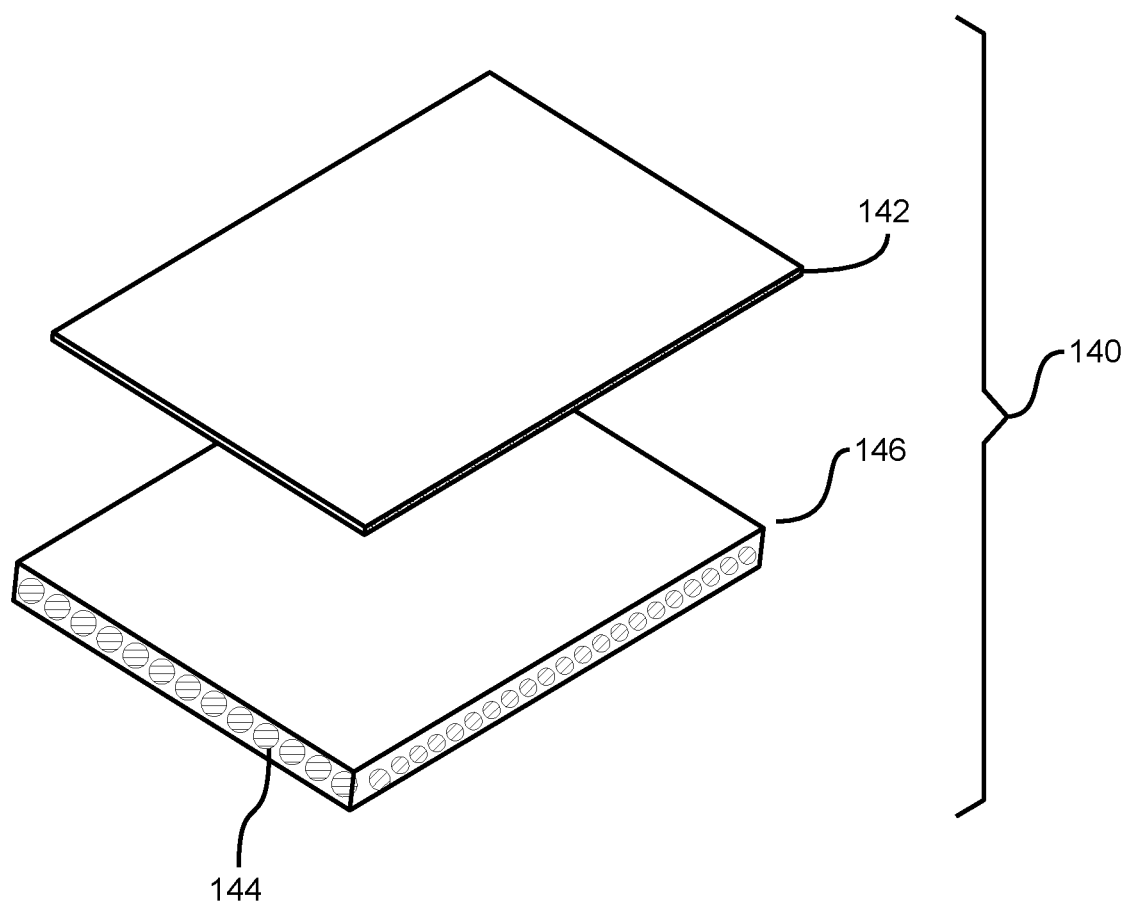
FIG. 2 represents a blood sample carrier in accordance with an embodiment of the invention.

FIG. 2 represents a blood sample carrier in accordance with an embodiment of the invention. The blood sample carrier is comprised of a sheet of absorbent paper 142 mounted on top of a desiccant bag 146. The absorbent paper typically has a uniform pore size, and can absorb a predetermined amount of liquid per area. Thus, storing a fixed amount of blood, plasma, or serum can be achieved by using a calculated size of absorbent paper. In addition, the paper of the carrier may be used in its entirety to recover the entire volume of blood sample stored therein, or the paper may be cut (e.g., punched) to collect a portion of the paper. The latter presents an advantage to the user for being able to use a portion of the paper and store the rest for subsequent use and/or use multiple cuts in separate tests in parallel to increase the statistical significance of the measurement.

Embodiments of the invention may utilize any available absorbent paper for carrying blood samples. For example, for use of commercially available glass fiber medium, the technical specifications are given in Table 1.

TABLE 1

| Property | Range | Ideal |
|---|---|---|
| Grammage, g/m$^2$ | 65-85 | 75 |
| Thickness, μm at 53 kPa | 310-390 | 350 |
| Porosity, sec/100 mis/0.1 square inch | 14-20 | 17 |
| M/D Dry Tensile, N/15 mm | min 9.0 | — |
| M/D Wet Tensile, N/15 mm | min 2.0 | — |
| Water Absorbency, % | 500-700 | 600 |
| Klemm, sec/4 cm | 30-50 | 40 |
| 98% Retention Efficiency, μm | 1.5-3.5 | 2.5 |

The blood sample carrier in accordance with embodiments of the invention comprises a layer of desiccant 146. The desiccant may be in the form of beads 144 contained in a bag (or any other type of container) provided it can be placed adjacently to the absorbent paper and allow for excess blood from a sample to liberally flow from the paper into the bed of desiccant.

The preferred desiccant is a molecular sieve. A molecular sieve is a material with uniform size pores, the diameter of which is similar in size to small molecules (e.g., water molecules). In an embodiment of the invention, 4A molecular sieve is used. 4A molecular sieve is a sodium aluminosilicate compound having a pore diameter of 4 Ångström, and it is known for its adsorption properties of water molecules. 4A molecular sieve is widely used in medical applications and it is approved for such use by the United States Food and Drug Administration (FDA).

By using a desiccant layer as an underlayment adjacent to the paper, specifically with properties to adsorb water molecule, the invention allows a user to be imprecise with the volume of blood deposited onto the paper. The goal of the invention is to allow the user to saturate the absorbent paper, then any extra volume of blood flows into the layer of desiccant. The volume of blood in the absorbent paper is retained by capillarity, while the water molecules as they evaporate during the drying stage are adsorbed by the desiccant. Therefore, the presence of the desiccant does not affect the volume of blood retained by the absorbent paper.

Numerous tests have been conducted to test embodiments of the invention. An analyte was selected for testing, and measurement were conducted on freshly collected blood samples and compared to test results conducted on dried blood after several days. The results are summarized in Table 2. In the latter tests, the analyte selected is Vitamin D, and the absorbent paper was 18×25 mm glass fiber medium. Composition of medium holds approximately 0.51 μL per mm$^2$. 230 μL of serum was added, dried, retained at ambient temperature for 3 days, and then extracted with 230 μL of Phosphate buffered saline (PBS). 25(OH)Vitamin D was tested on extraction fluid and compared to the initial measurement.

TABLE 2

| Molecular Sieve Type | Number of Measurements | Avg. Vitamin D (ng/ml) | STD | CV |
|---|---|---|---|---|
| 4A Sieve-Small | 4 | 47.3 | 1.8 | 4% |
| 4A Sieve-Small | 5 | 48.4 | 2.1 | 4% |
| 4A Sieve-Small | 5 | 125.5 | 6.8 | 5% |
| 13x Sieve-Medium (1) | 5 | 126.5 | 2.9 | 2% |
| 13x Sieve-Medium (1) | 5 | 69.7 | 4.2 | 6% |
| 13x Sieve-Medium (1) | 5 | 60.2 | 2.1 | 3% |
| 13x Sieve-Medium (1) | 5 | 60.5 | 1.8 | 3% |

Intra-assay precision ranged from 2-6% CV which is within the precision of the assay itself demonstrating 230 μL was retained within the medium. (1) The volume deposited exceed the 230 μL and ranged between 230 μL and 400 μL. Intra-assay precision ranged from 3-7% CV which is within the precision of the assay itself demonstrating 230 μL was retained within the medium even when excess volume was applied to the glass fiber medium.

Further tests were carried out to test the precision of "wick-away" or differential capillary action on volume retention using glass fiber medium and varying amounts of serum applied. Type 13x (medium) molecular sieve was used with 18×25 mm glass fiber medium. Composition of medium holds approximately 0.51 μL per mm². 230 μL to 400 μL of serum was added, dried, retained at ambient temperature for 3 days, and then extracted with 230 μL of PBS. The use of imprecise disposable transfer pipettes were used to evaluate such methods. 25(OH)Vitamin D was tested on extraction fluid and compared. The results are summarized in Table 3.

TABLE 3

| Molecular Sieve Type | Number of Measurements | Avg. Vitamin D (ng/ml) | STD | CV |
|---|---|---|---|---|
| 13x Sieve-Medium (1) | 7 | 97.9 | 4.8 | 5% |
| 13x Sieve-Medium (1) | 8 | 53.8 | 1.8 | 3% |
| 13x Sieve-Medium (1) | 8 | 31.9 | 2.4 | 7% |

Intra-assay precision ranged from 3-7% CV which is within the precision of the assay itself demonstrating 230 μL was retained within the medium even when excess volume was applied to the glass fiber medium.

Multi-Sample Device for Collecting and Preserving Blood Samples

Figure 3:
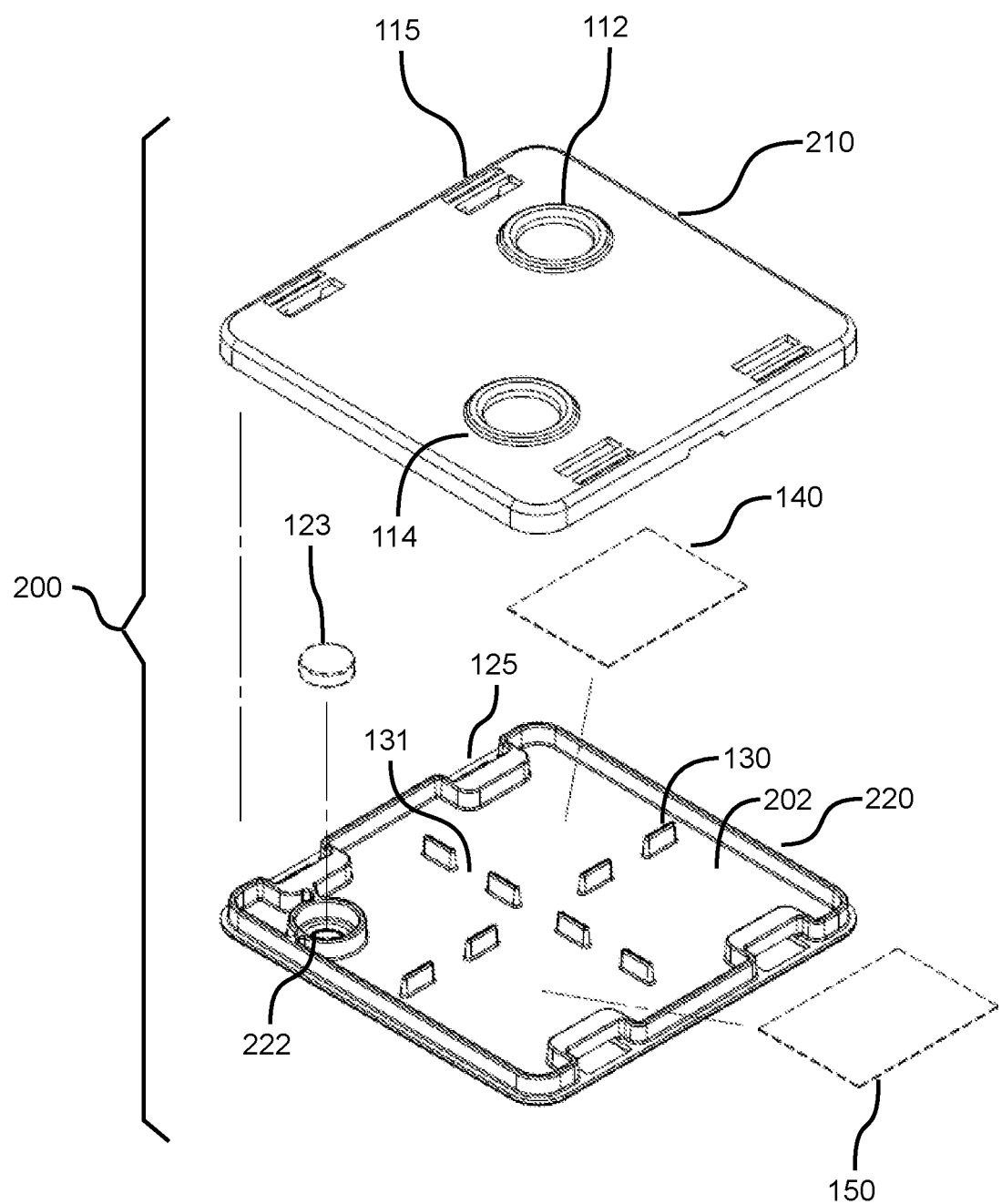
FIG. 3 represents an exploded perspective view of a device for receiving freshly collected blood samples and for drying and storing multiple samples in accordance with an embodiment of the invention.

FIG. 3 represents an exploded perspective view of a device for receiving freshly collected blood samples and for drying and storing multiple samples in accordance with an embodiment of the invention. As with the device illustrated in FIG. 1, device 200 according to the invention comprises a top lid 210, and a bottom lid 220, that are configured to lock to one another to provide an enclosure 202.

The top lid 210 has two (2) windows for allowing access to enclosure 202, where two blood sample carriers 140 and 150 may be placed at once. Embodiments of the invention may be designed with more than two (2) holding areas for blood sample carriers, and access windows for depositing and drying the blood samples.

In addition, FIG. 3 shows that the bottom lid may be configured to comprise a well 122 for receiving an oxygen level indicator 123. Oxygen level may be color coded and can be visibly inspected through a window 223 (shown in FIG. 5) in the bottom of the bottom lid 220.

Figure 4:
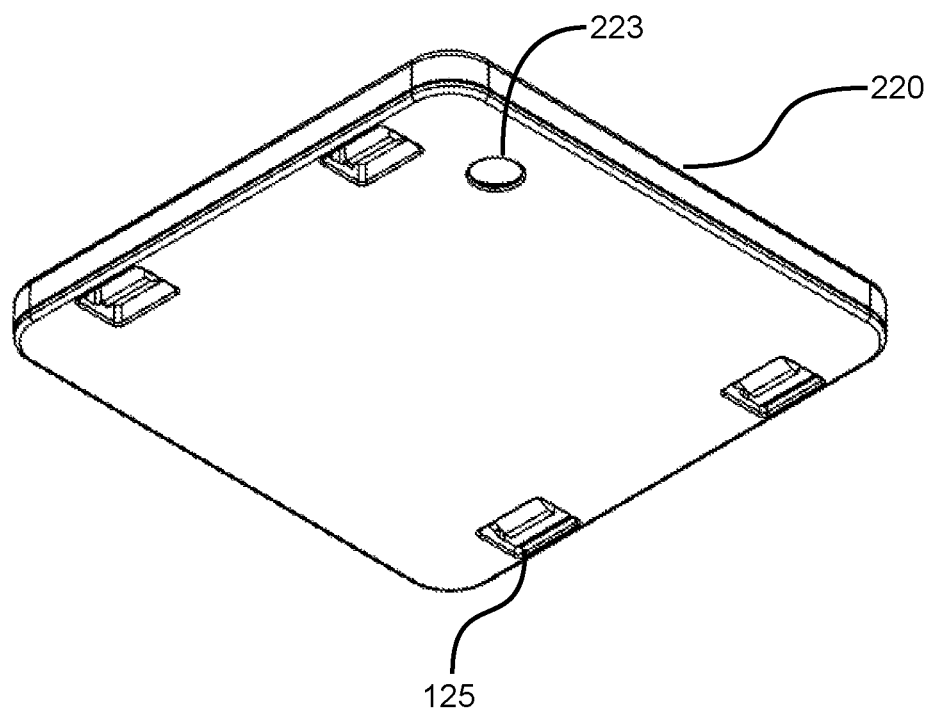
FIG. 4 represents a bottom perspective view of a bottom lid of a device for receiving freshly collected blood samples and for drying and storing blood samples in accordance with an embodiment of the invention.

FIG. 4 represents a bottom perspective view of a bottom lid of a device for receiving freshly collected blood samples and for drying and storing blood samples in accordance with an embodiment of the invention. Opening 223 represents visible access to an oxygen indicator for accessing the oxygen level with the device's enclosure.

Figure 5:
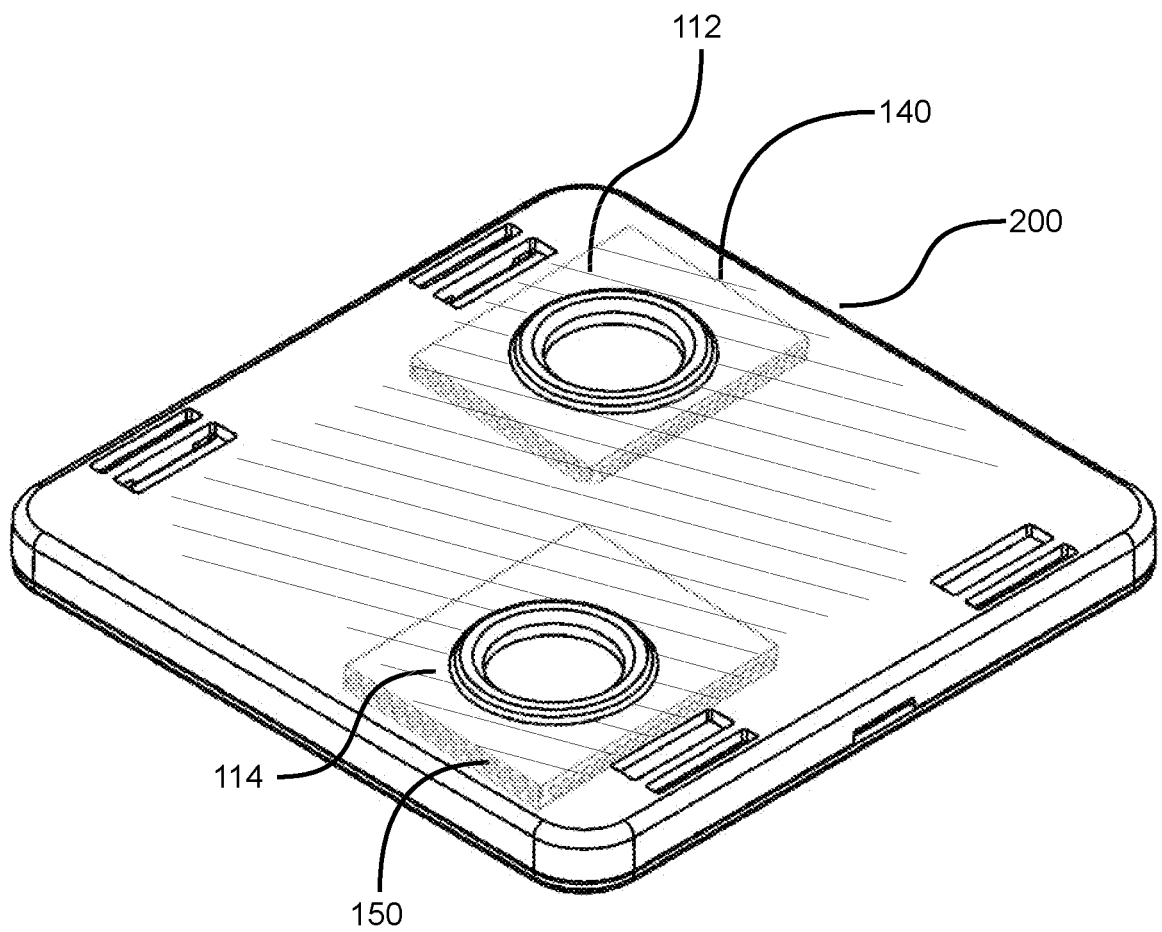
FIG. 5 represents a top perspective view of an assembled device for receiving freshly collected blood samples and for drying and storing multiple samples in accordance with an embodiment of the invention.

FIG. 5 represents a top perspective view of an assembled device for receiving freshly collected blood samples and for drying and storing multiple samples in accordance with an embodiment of the invention. Two (2) blood sample carriers 140 and 150 are securely held within the enclosure, under each of the windows 112 and 114 to allow access for depositing fresh blood samples, and promote drying of the blood.

Figure 6:
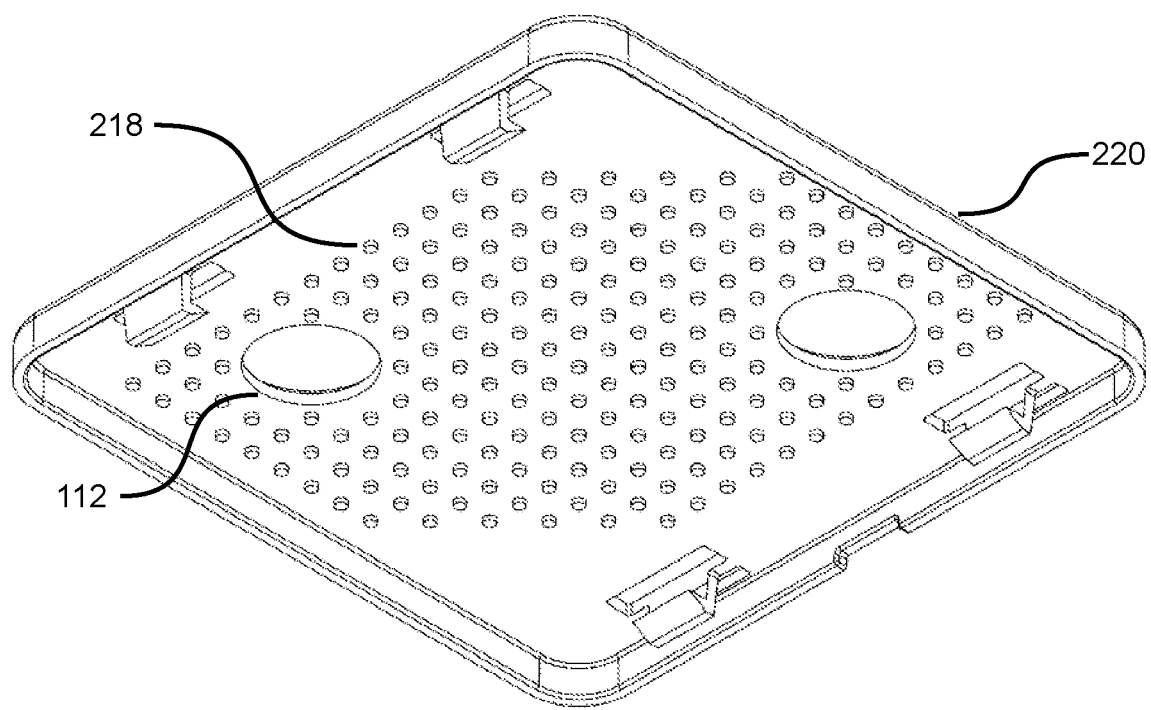
FIG. 6 represents a bottom perspective view of the top lid of a device for receiving freshly collected blood samples and for drying and storing multiple samples in accordance with an embodiment of the invention.

FIG. 6 represents a bottom perspective view of the top lid of a device for receiving freshly collected blood samples and for drying and storing multiple samples in accordance with an embodiment of the invention. Absorbent paper is lifted off the plastic enclosure by the addition of small raised numbs 218 to further aid air flow between the absorbent paper and desiccant, thus minimizing contact with the inner walls of the enclosure and aid in fast drying.

Modified Atmospheric Packaging

The invention was developed with the working hypothesis that the presence of oxygen, a highly reactive oxidative species, can alter organic compound structure and lead to degradation of blood analytes during storage and/or transportation.

Embodiments of the invention achieve the stabilization of analytes in blood samples by removing a substantial portion of the water and oxygen from the blood sample, and maintaining such an environment in which the blood sample is stored until the blood sample is extracted/recovered for testing.

The invention provides a modified atmospheric packaging (MAP), which is designed to maintain a low $O_2$ environment while in transit from the customer to the laboratory. However, with atmospheric $O_2$ at 21%, maintaining a low $O_2$ level (e.g., less than 0.1%) is challenging. As stated above, the latter challenge is addressed in the food industry by the use of foil and/or impermeable plastic bags that are simply heat sealed. Heat sealing is not a reliable option due to typical lack of the equipment (or easy access thereto) required for sealing.

The invention solves this problem through the use of an impermeable material such as foil or plastic (e.g., Mylar), a dual-track zip lock and a seal adhesive glue over flap. The combination of these barriers maintain a very low $O_2$ level (<0.1%) for 21 days.

Figure 7:
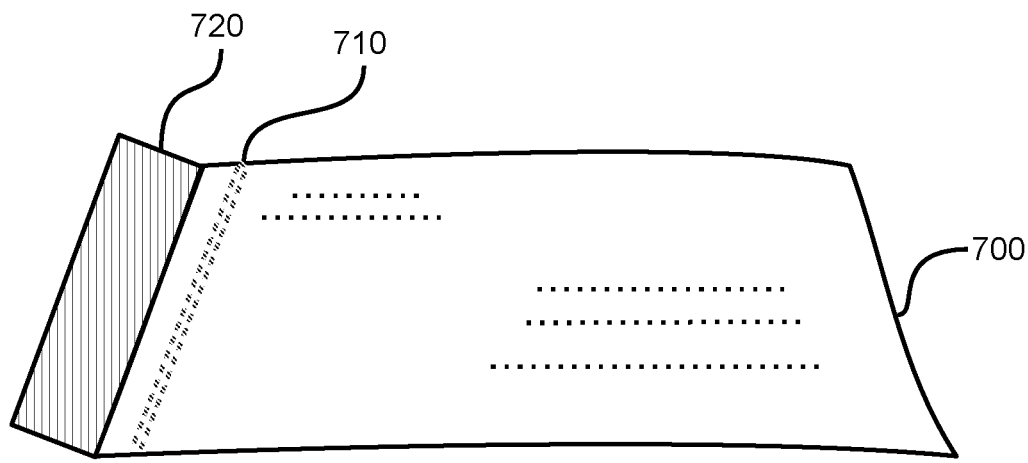
FIG. 7 represents a sealable bag for providing storage and transportation of blood sample devices in accordance with an embodiment of the invention.

FIG. 7 represents a sealable bag for providing storage and transportation of blood sample devices in accordance with an embodiment of the invention. Shipping bag/container 700 may be made of foil, plastic or any other material suitable for fabricating a container (e.g., Mylar) that is impermeable to moisture and air/oxygen. The bag 700 is provided with one or two zipping mechanisms 710 for tightly closing the bag. The locking typically consists of interlocking groove and ridge that form a tight seal when pressed together. In addition bag 700 is provided with a flap 720 that may be folded onto bag 700 and glued thereto.

A bag according to the invention may be designed to meets postal services regulations for shipping by postal mail (or any other parcel carrier services). For example, for letter rate mail (e.g., weight, size, labeling, machine sorting process capable), bag 700 may be designed for the regulations of the United States Postal Services.

Moreover, after a blood sample is placed onto the synthetic paper it is inserted into bag 700, an oxygen scavenger (e.g., iron filings) is introduced in the bag to remove the free oxygen within the bag after the bag has been sealed.

MAP according to the invention was evaluated for over 21 days by two different methods: 1) by the use to thymidine kinase type 1, an enzyme known to be unstable when dried and exposed to oxygen; and 2) an oxygen indicator, an indicator that turns pink when $O_2$ levels are below 0.05%; purple when $O_2$ levels are above 0.05%.

Figure 8:
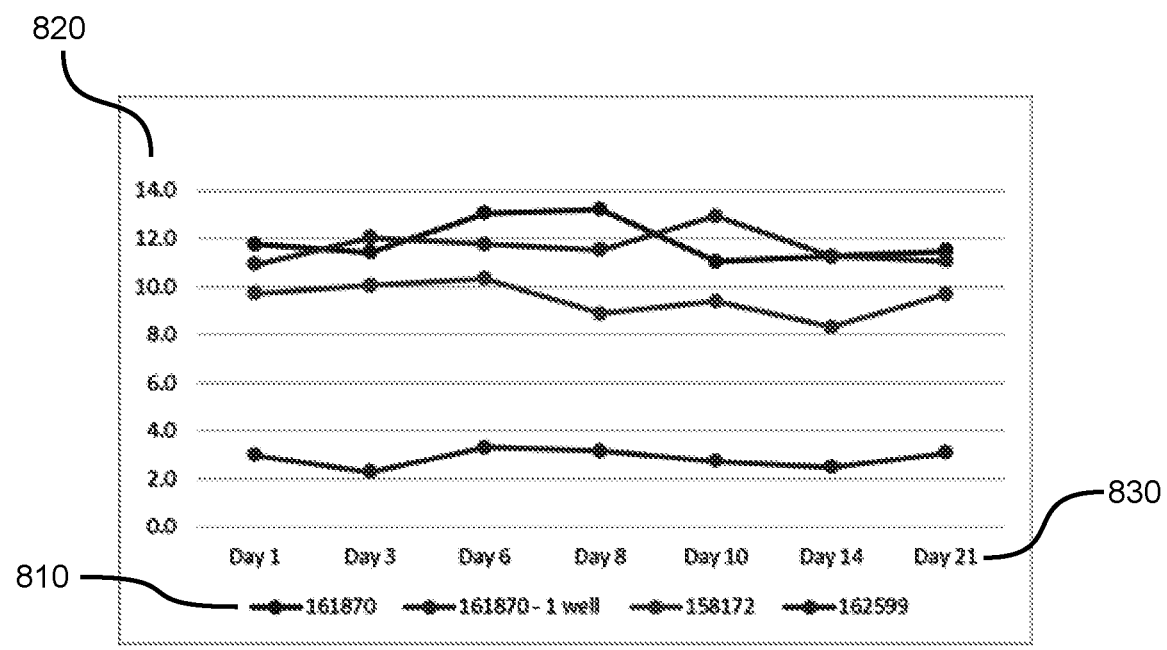
FIG. 8 graphically represents test results obtained for thymidine kinase tested in four (4) subjects for a period lasting up to twenty one days.

FIG. 8 graphically represents test results obtained for thymidine kinase tested in four (4) subjects for a period lasting up to twenty one days. Thymidine kinase was measured in four subjects 810 in freshly collected blood samples and from dried samples that have been stored for up to 21 days 830. Thymidine kinase levels measurements 820 show that, when compared to itself, the level remained virtually constant.

Moreover, an oxygen indicator was placed within blood collection and storage device and the level of oxygen visually inspected using the color scale of the oxygen indicator. The results show in four (4) tested subjects that the indicator had a pink color each day the samples were inspected, which was on day 1, 3, 6, 8, 10, 14 and 21.

Thus, a device and system for preserving analytes in blood samples during storage and transportation.

The claimed invention is:

1. A device for drying blood, and preserving analytes in dried blood samples during storage and transportation comprising:
    at least one blood sample carrier comprises a sheet of an absorbent matrix having a uniform pore size, and able to absorb a predetermined amount of liquid per area, thus allowing for recovery of a fixed amount of dried blood sample per area of said absorbent matrix, wherein a calculated area of said sheet of said absorbent matrix is used to store a fixed amount of blood, wherein said sheet of absorbent matrix is punched into two or more cuts, wherein each of the two or more cuts is used in a separate test to increase statistical significance of measurements;
    a desiccant layer mounted as an underlayment adjacent to said absorbent matrix, wherein said desiccant layer is a molecular sieve having properties to adsorb water molecules, wherein said molecular sieve is a sodium aluminosilicate compound having a pore diameter of 4 Angstrom;
    a box comprised of a top lid and a bottom lid, wherein said top lid and bottom lid are configured to lock to one another to provide an enclosure for receiving said at least one blood sample carrier; and
    a plurality of holding areas separated by ridges and further having channels for air circulation within said enclosure for holding said at least one blood sample carrier.

2. The device of claim 1, wherein said box is made of plastic.

3. The device of claim 1, wherein said box is made of metal.

4. The device of claim 1, wherein said top lid and bottom lid have matching rectangular shapes.

5. The device of claim 1, wherein said top lid and bottom lid have matching square shapes.

6. The device of claim 5, wherein said top lid and bottom lid have a matching square shape with a side dimension in the range of 2 inches to 3 inches.

7. The device of claim 6, wherein said top lid and bottom lid have a matching square shape with a side dimension of 2.3 inches and a thickness of 0.2 inch.

8. The device of claim 1, wherein said top lid further having at least one window for allowing a user access to said blood sample carrier to deposit a blood sample thereon.

9. The device of claim 1, wherein said absorbent matrix is a 18×25 mm glass fiber medium configured to hold 230 µL of liquid.

10. The device of claim 9, wherein said desiccant is a four (4) Angstrom pore size molecular sieve for adsorbing water molecules evaporated from 400 µL.

11. The device of claim 1, wherein said enclosure further comprises an oxygen sensor for detecting a level of oxygen in the air within the box, and a window through said box to allow for visually inspecting said oxygen sensor.

12. The device of claim 11, wherein said oxygen sensor has a color pink when the surrounding level of oxygen is below 0.05%, and has the color of purple when the oxygen level is 0.05%.

13. A system for drying blood, and preserving analytes in dried blood samples during storage and transportation comprising:
    a device for receiving and storing blood samples comprising:
        at least one blood sample carrier comprises a sheet of an absorbent matrix having a uniform pore size, and able to absorb a predetermined amount of liquid per area, thus allowing for recovery of a fixed amount of dried blood sample per area of said absorbent matrix, wherein a calculated area of said sheet of said absorbent matrix is used to store a fixed amount of blood, wherein said sheet of absorbent matrix is punched into two or more cuts, wherein each of the two or more cuts is used in a separate test to increase statistical significance of measurements;
        a desiccant layer mounted as an underlayment adjacent to said absorbent matrix, wherein said desiccant layer is a molecular sieve having properties to adsorb water molecules, wherein said molecular sieve is a sodium aluminosilicate compound having a pore diameter of 4 Angstrom;
        a box comprised of a top lid and a bottom lid, wherein said top lid and bottom lid are configured to lock to one another to provide an enclosure for receiving at least one blood sample carrier; and
        at least one holding area within said enclosure for holding said at least one blood sample carrier; and
    a modified atmosphere container comprised of an impermeable bag and containing therein a bag of an oxygen scavenging compound.

14. The system of claim 13, wherein said impermeable bag further comprises a Mylar bag.

15. The system of claim 13, wherein said Mylar bag is configured with a dual-track zip lock and a seal adhesive glue over flap.

16. The system of claim 13, wherein said oxygen scavenging compound comprises iron filings.

17. The system of claim 13, wherein said absorbent matrix comprises an absorbent paper.

18. The system of claim 13, wherein said absorbent matrix comprises a glass fiber medium.

* * * * *